United States Patent [19]
Bassett

[11] 3,946,740
[45] Mar. 30, 1976

[54] SUTURING DEVICE
[76] Inventor: John W. Bassett, 2231 Lloyd Center, Portland, Oreg. 97232
[22] Filed: Oct. 15, 1974
[21] Appl. No.: 514,578

[52] U.S. Cl. .............................. 128/334 R; 128/340
[51] Int. Cl.² ......................................... A61B 17/04
[58] Field of Search ........ 128/326, 334 R, 340, 321, 128/322, 346

[56] References Cited
UNITED STATES PATENTS

| | | | |
|---|---|---|---|
| 1,037,864 | 9/1912 | Carlson et al. | 128/340 |
| 1,293,565 | 2/1919 | Smit | 128/340 |
| 1,449,087 | 3/1923 | Bugbee | 128/340 |
| 3,470,875 | 10/1969 | Johnson | 128/340 X |
| 3,807,407 | 4/1974 | Schweizer | 128/340 X |
| 3,842,840 | 10/1974 | Schweizer | 128/334 R |

Primary Examiner—Dalton L. Truluck
Attorney, Agent, or Firm—Kolisch, Hartwell, Dickinson & Stuart

[57] ABSTRACT

A suturing device including a pair of arms having a set of adjacent ends movable toward and away from each other for engaging opposite sides of tissue therebetween. One of the arms has a needle-holding channel formed therein which opens at one end in the direction of the other arm. A manually operable needle driving member is mounted for movement on the one arm to drive a needle from the channel, through the tissue, and into the region of the other arm. The other, or second, arm has a needle receiving chamber therein for receiving the pointed end of the needle driven through the tissue. A rotatable needle holding element adjacent the needle receiving chamber is shiftable between a release position permitting entry of the needle into the chamber and a holding position in which it grips and holds the needle in the chamber. The needle holding element is operatively connected to a manually operable handle mounted on the second arm, which handle is shiftable between released and holding positions for producing corresponding shifting of the holding element. The operator handle is spring biased from its release toward its holding position, following initial displacement from its release position. A tissue engaging element mounted on the second arm is operable to engage and force tissue over the shank of the needle to insure full passage of the needle through the tissue when the arms are swung away from each other. A needle retracting device on the first arm is operable to receive and grip a needle when the driving element is extended, and on retraction of the driving element grips the needle to draw it into the needle holding channel.

14 Claims, 14 Drawing Figures

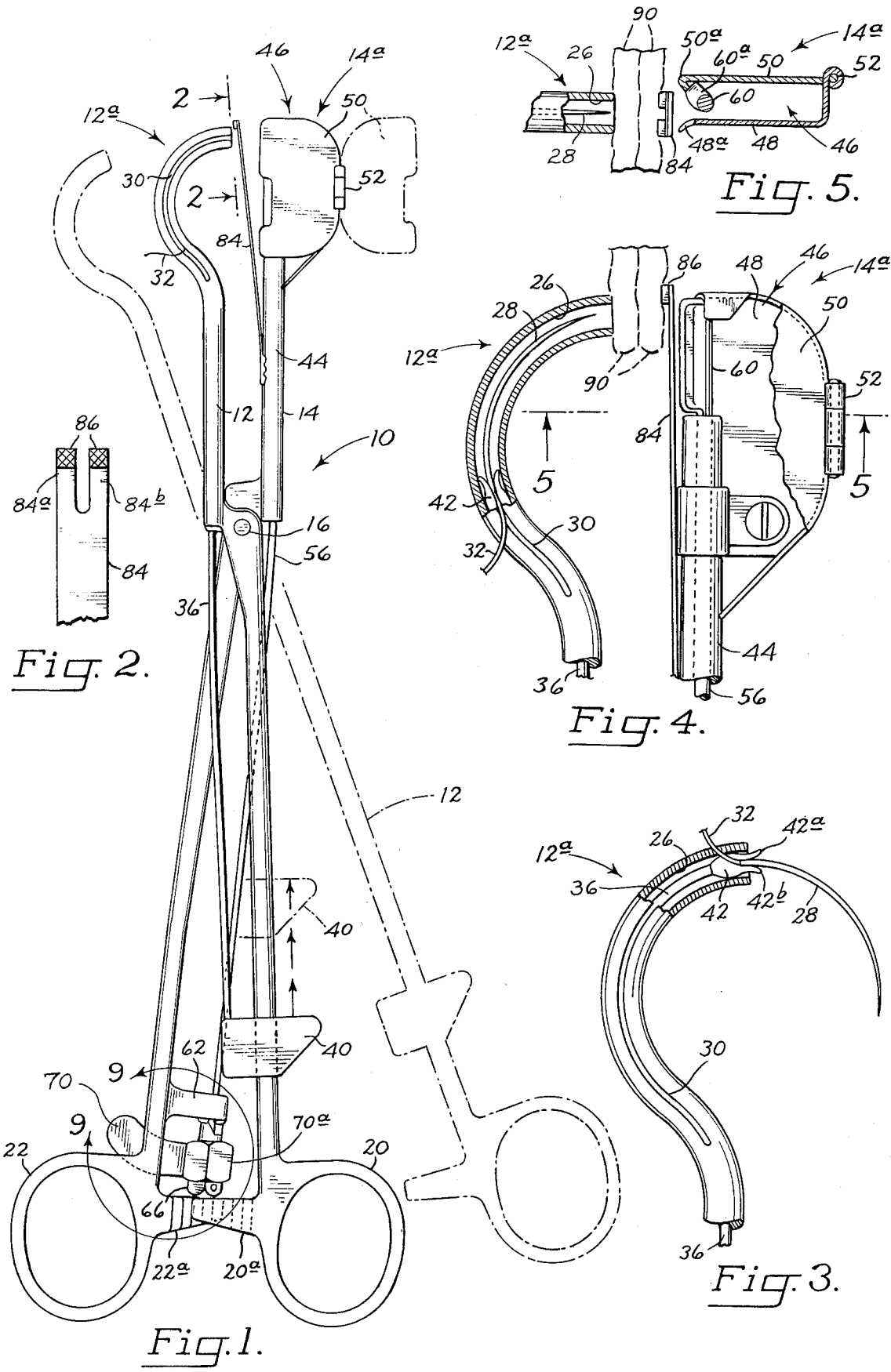

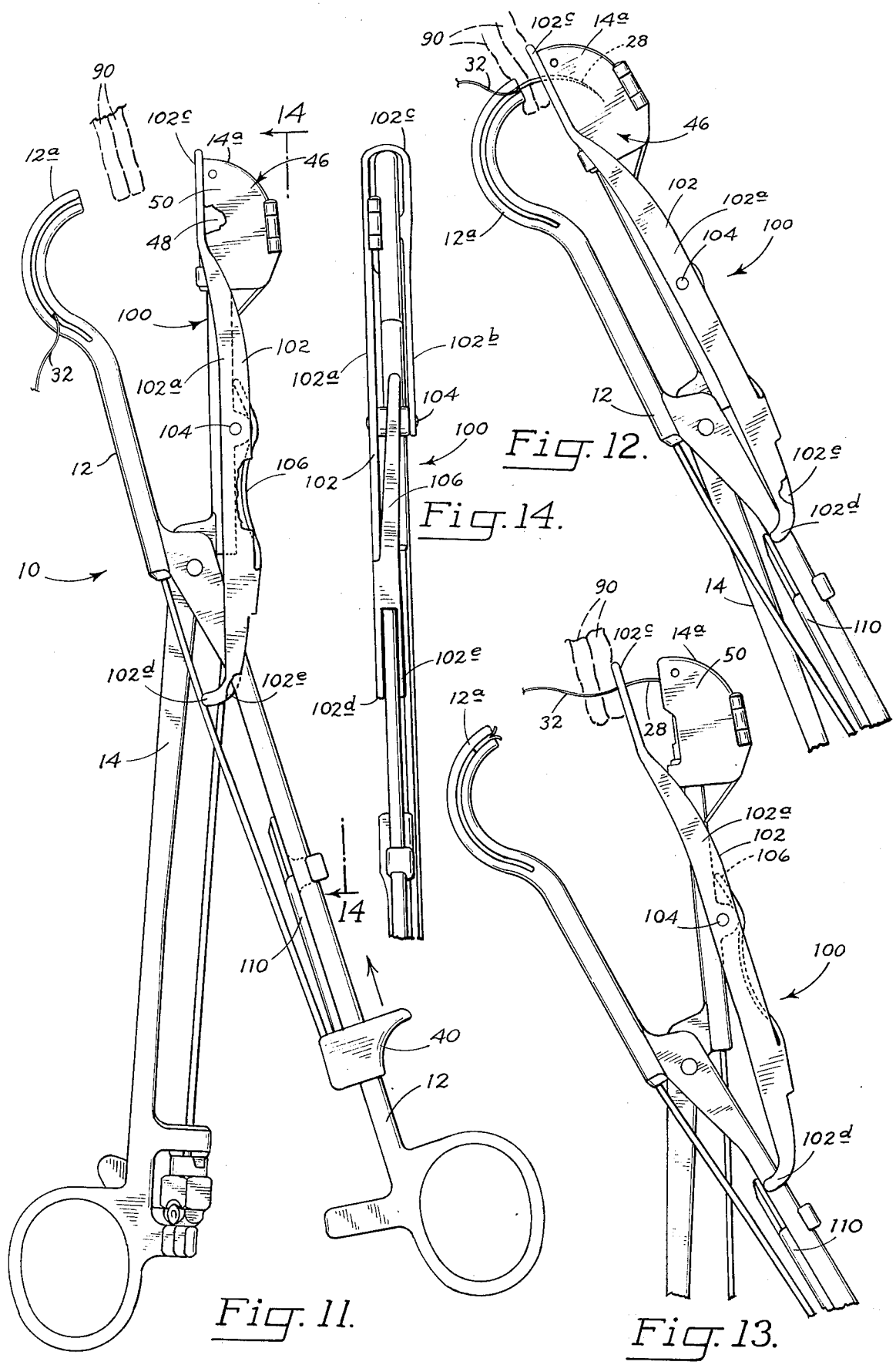

SUTURING DEVICE

BACKGROUND AND SUMMARY OF THE INVENTION

This invention relates to a suturing device operable to pass a needle through tissue, grasp the needle on the opposite side of the tissue, with gripping of the needle on the opposite side of the tissue being selectively produced by the operator from a region distant from the needle, and permitting withdrawal of the needle thus gripped from the tissue.

Various suturing devices have been devised in the past, however, for the most part, these have been rather complex devices which have been rather cumbersome to use and complex in their construction. Further, such previous devices generally have not had provision for driving a needle through tissue, and then selectively gripping the needle on the opposite side of the tissue to draw the needle fully through the tissue and withdraw it from the area of the tissue. Prior suturing devices also have lacked convenient means for loading a needle therein for operation.

A general object of the present invention is to provide a novel suturing device which overcomes the above set out disadvantages of prior known devices in a simple and economical manner.

More specifically, an object of the present invention is to provide a novel suturing device including a pair of elongate arms having an adjacent set of ends swingable toward and away from each other for gripping tissue therebetween. One of the arms has needle driving means thereon for driving a needle through the tissue and into the region of the other arm. The other arm has a needle holding element thereon which is selectively shiftable between a release position which permits passage of the needle freely into the region of the other arm, and a holding position in which the needle is gripped by the other arm. After passage of the needle through the tissue and gripping of the needle in the other arm, the arms may be spread apart, to fully draw the needle through the tissue and the device then is withdrawn from the tissue.

Such a device may be of particular advantage to surgeons who may have to suture tissue within a region which is not only difficult to reach, but also is obscured from view. With such a device, the surgeon may insert the operating ends of the arms into the region of the tissue to be sutured, operate the device to drive the needle through the tissue, after the needle has been driven through the tissue grip it in the holding means, and then pull it through the tissue on spreading the arms apart, and thereafter withdraw it from the region.

Another object of the present invention is to provide such a device wherein an operator handle for producing shifting of the needle holding means is positioned on one of the arms in a region spaced from the operating ends of the device, thus to permit manual actuation thereof by the user in a region spaced from the operating ends. This allows for selectivity of operation of the holding member, wherein the same does not grip a needle until such time as the user actuates the operating handle.

Yet another object of the present invention is to provide such a novel device wherein the operator handle is shiftable between released and holding positions and is operatively connected to the holding member for producing corresponding movement thereof between its release and holding positions, and which further includes yieldable biasing means operable to urge the operator handle toward its holding position after initial displacement thereof from its release position. With such construction once the operator handle is initially shifted from its release position the biasing means will operate to urge the holding member to its gripping position.

A still further object of the present invention is to provide a suturing device having a needle holding channel in one of its arms opening at one of its ends in the direction of the other arm, and including needle retracting means operable to receive and grip a needle and, upon operation to retract the needle to draw it into the channel. Not only is this a benefit in initially loading the device for use, but also permits the user, during operation, to retract the needle even after it has been forced partially through tissue.

Another object is to provide in a suturing device tissue shifting means which is operable to engage and shift tissue fully over the shank of a needle to assure full passage of the needle through the tissue before withdrawal of the device.

DRAWINGS

These and other objects and advantages of the present invention will become more fully apparent as the following description is read in conjunction with the drawings wherein:

FIG. 1 is a view of a suturing device constructed according to an embodiment of the invention;

FIG. 2 is an enlarged view taken generally along the line 2—2 in FIG. 1 of an end of tissue engaging means in the device;

FIG. 3 is an enlarged view of the operating end of an arm in the device with portions broken away to illustrate needle driving and retracing means therein;

FIG. 4 is an enlarged view of adjacent operating ends of opposed arms in the device with portions broken away to illustrate a needle loaded therein and tissue gripped between the operating ends;

FIG. 5 is a cross-sectional view taken generally along the line 5—5 in FIG. 4;

FIG. 11 is a view of a suturing device according to the invention including modified tissue engaging means, with the operating ends of the device spread apart and the tissue engaging means positioned to receive tissue therebetween;

FIG. 12 is a view of a portion of the device of claim 10 with the operating ends closed to grip tissue therebetween, and needle driving means shifted forwardly to drive a needle through tissure.

FIG. 13 is a view of the device of FIG. 10 with the operating ends of the device spread apart and the tissue engaging means operating to force tissue over the shank of a needle; and FIG. 14 is a view of the device taken generally along the line 14—14 in FIG. 11.

DETAILED DESCRIPTION OF AN EMBODIMENT OF THE INVENTION

Figure 7:
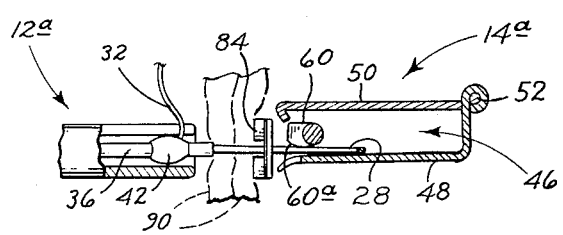
FIG. 7 is a cross-sectional view taken generally along the line 7—7 in FIG. 6.

Referring to the drawings, and first more particularly to FIG. 1, at 10 is indicated a suturing device constructed according to an embodiment of the invention. The device includes a pair of elongate arms 12, 14 pivotally interconnected at 16 intermediate their ends for swinging relative to each other.

Finger rings 20, 22 are formed at the rear ends of arms 12, 14 respectively. Such finger rings are engagable by the thumb and a finger of an operator's hand for swinging the arms relative to each other about pivot 16. Projections 20a, 22a on rings, 20, 22 respectively project toward each other and have ratchet teeth on their facing surfaces which lock in to each other when the rings, or handle portions, are swung into closely spaced relation, as illustrated in FIG. 1. The ratchet teeth may be released for swinging relative to each other by shifting the handles and projections laterally outwardly from each other to disengage the teeth.

The opposite, or operating, ends 12a, 14a of arms 12, 14, respectively, are spaced on the opposite side of pivot 16 from rings 20, 22. The operating ends of the arms are swingable toward and away from each other concurrently with swinging of rings 20, 22 toward and away from each other, as is illustrated by the solid and dot-dash positions for arm 12 in FIG. 1.

Describing the operating end 12a of arm 12, and referring to FIGS. 3 and 4, it will be seen that it includes an elongate, tubular member having a cylindrical interior, needle holding channel 26 formed therein. The channel is open at its end directed toward the opposite arm 14a. The device illustrated is for use with arcuate suturing needles, such as that indicated generally at 28, and thus channel 26 is curved in an arc corresponding generally to the curvature of such a needle.

Such a needle generally would have a thread, such as that indicated at 32, secured to a shank portion of the needle. An elongate slot 30 extending longitudinally along one side of the tubular member into channel 26 permits passage of thread 32 therethrough.

An elongate needle driving member 36 extends from a substantially adjacent finger ring 20 on arm 12, through a major portion of channel 26, and is mounted for movement longitudinally in the channel and relative to handle 12. The portion of driving member 36 which extends through and is slidable within the arcuate portion of channel 26 has a degree of flexibility which allows it to conform to the arcuate shape of the channel, yet still has sufficient columnar strength that it can shove needle 28 through tissue, as will be described in greater detail below. The remainder portion of driving member 36, which extends along handle 12, is suubstantially rigid and has sufficient columnar strength throughout its length whereby it also may support needle driving force exerted thereagainst in a direction longitudinally of the member without buckling. A slide member 40 secured to the rear end of member 36 is mounted for sliding movement on arm 12. Manual shifting of member 40 from the retracted position illustrated in solid outline in FIG. 1 to the extended position illustrated in dot-dash outline, moved forwardly along arm 12 acts to force driving member 36 between the retracted position illustrated in FIG. 4 and the extended position illustrated in FIG. 3.

Secured to the forward end of member 36 (see FIG. 3) is a needle gripping, or retracting, member 42. Member 42 has a pair of opposed leg portions 42a, 42b which are yieldably biased outwardly and away from each other toward the position illustrated in FIG. 3. When the needle driving member 36 is in its extended position as illustrated in FIG. 3, leg portions 42a, 42b project outwardly beyond the end of channel 26 are spread apart, and thus are adapted to receive a shank portion of needle 28 therebetween. Upon retraction of driving member 36 and entry of gripping member 42 into channel 26, the sides of the channel force legs 42a, 42b toward each other to grip the needle, with further retraction of the gripping member producing retraction of the needle fully into the channel, as is illustrated in FIG. 4, with its pointed end directed toward the opposite operating arm 14a. As the needle is retracted into channel 26 thread 32 may travel therewith through slot 30.

Operating end 14a of arm 14 includes an elongate, tubular section 44 at the outer end of which is secured a needle receiving chamber indicated generally at 46. The chamber is defined by a pair of spaced side walls 48, 50 hingedly interconnected at 52 to permit opening of the chamber as illustrated generally in dot-dashed outline in FIG. 1 to facilitate cleaning and other operation. Releasable fastening means is operable to hold wall 50 in its closed position, as illustrated in solid outline, throughout normal operation.

As is best seen in FIG. 5, the opposed, laterally spaced, edge margins 48a, 50a of walls 48, 50, respectively, diverge on progressing outwardly from chamber 46 toward arm 12 and thus form a guiding entry way through which needle 28 may pass from channel 26 into chamber 46.

Referring to FIGS. 1 and 4, an elongate, cylindrical rod 56 extends longitudinally and rotatably through the bore extending through tubular section 44 of arm 14. Secured to the forward end extremity of rod 56 for rotation therewith is an elongate needle holding member 60 (see FIGS. 4 and 5). Member 60 has a lobe 60a which is mounted for rotation, or pivoting, about an axis spaced laterally of the path along which needle 28 would pass upon being driven from channel 26 into chamber 46. On rotation, the lobe moves from a released, or inoperative, position as illustrated in FIG. 5 directed away from side wall 48, and a holding, or operative position, indicated generally in FIG. 7, rotated toward wall 48. As is seen in FIG. 5, when in its released position, the lobe on the needle holding member provides an extension of wall edge margin 50a directed inwardly toward chamber 46 to aid in guiding a needle as it passes from channel 26 toward chamber 46. With the lobe in its holding position, as seen in FIG. 7, it is operable to press a needle against side wall 48 of the chamber and thus grip and hold the needle therebetween.

Figure 9:
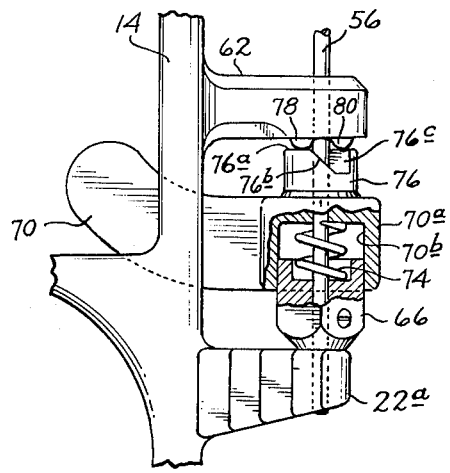
FIG. 9 is an enlarged view of an operating member taken generally in the region of line 9—9 in FIG. 1, with portions broken away.

Rod 56 is journalled for rotation in a bearing post 62 secured to arm 14 adjacent finger ring 22 and at its rear extremity is journalled in a bore extending through projection 22a (see FIG. 9).

Figure 10:
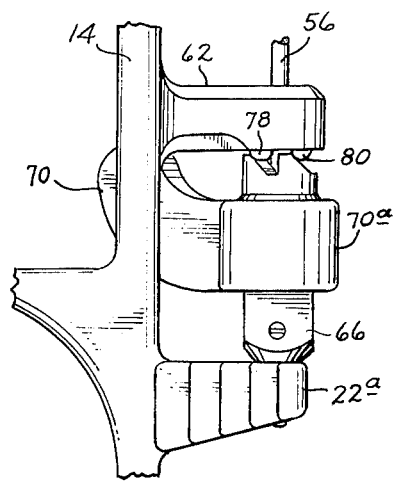
FIG. 10 is a view somewhat similar to FIG. 9, but with the operating handle shifted from its holding position, illustrated in FIG. 9, toward a release position.

Referring to FIGS. 1, 9, and 10, a member 66 having a square cross-section when viewed longitudinally of rod 56 is secured to the rod intermediate post 62 and projection 22a for rotation with rod 56. An elongate operating lever 70 has a base portion 70a which is mounted slidably on rod 56 for movement longitudinally along the rod. The base portion 70a also has a square cavity 70b formed therein which receives member 66 in such a manner that lever 70 is slidable longitudinally of rod 56 on member 66, but rotation of lever 70 about the longitudinal axis of rod 56 serves to rotate member 66 and rod 56. A compression spring 74 interposed between member 66 and lever base 70a yieldably urges the lever forwardly toward bearing post 62.

Secured to the forward surface of base portion 70a is a cam member 76 which encircles rod 56. The cam member includes a flat forwardly facing surface 76a, a sloping face 76b, and an upright side wall 76c opposite, and spaced circumferentially from face 76b. A pair of spaced projections 78, 80 are formed on the rearwardly facing surface of post 62. Projections 78, 80 are so positioned that when lever arm 70 is in the release position illustrated in FIG. 9 and holding member 60 is in its release position as illustrated in FIG. 5, a projection, such as indicated at 80, engages the upper marginal edge of side wall 76c to initially inhibit rotation of the lever in a direction away from the viewer in FIG. 9. This yieldably holds the operating lever and holding member 66 in their release positions. Forcing operating lever 70 away from the viewer in FIGS. 1 and 9 causes base portion 70a of the lever to shift rearwardly to pass under a projection with sloping face 76b then coming into contact with the projection. With spring 74 urging the operating lever forwardly the sloping face of cam member 76 coacts with the projection to yieldably urge the operating lever and holding member 60 to rotate in a direction away from the viewer to the holding position illustrated in FIG. 10. In this holding position the needle holding member is in its operative position as illustrated in FIG. 7.

Figure 8:
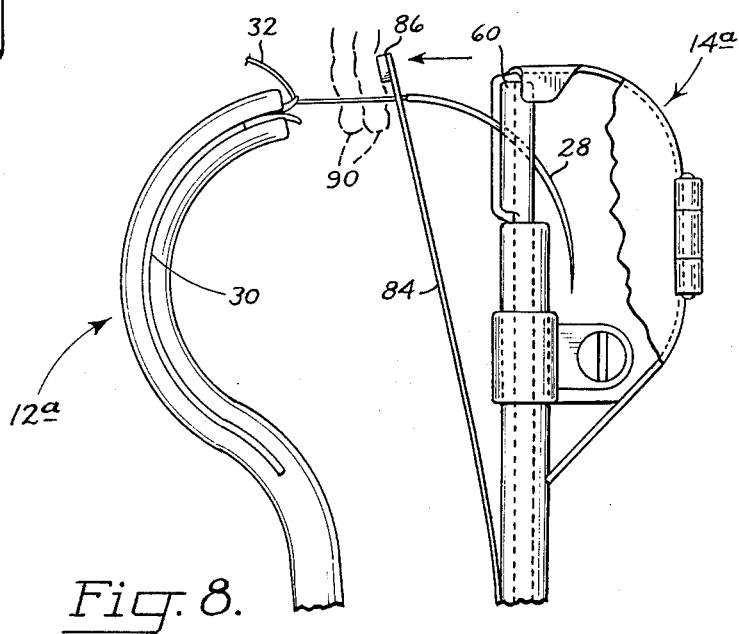
FIG. 8 is a view of the operating ends of the device somewhat spread apart.

Referring to FIGS. 1, 2 and 8, at 84 is illustrated an elongate, tissue shifting member. In the embodiment illustrated, member 84 is an elongate strip of spring steel secured at one of its ends to arm 14 with its other end interposed between the forwardmost end portions of operating ends 12a, 14a of the arms.

As is seen in FIG. 2 the forward end portion of member 84 is bifurcated producing legs 84a, 84b to which are secured engaging pads 86. The tissue engaging member is so positioned in the device that legs 84a, 84b are disposed on opposite sides of the path along which a needle 28 may pass on being shifted from channel 26 in operating head 12a into chamber 46 on operating head 14a. The construction of tissue shifting member 84 is such that it is movable with arm 14, but its outer end bearing legs 84a, 84b is yieldably biased outwardly from arm portion 14a toward the normally at rest position illustrated in solid outline in FIG. 1.

Describing the operation of the device as it might be used by a surgeon to suture tissue, the arms 12, 14 are rotated away from each other as illustrated in dot-dash outline for arm 12 in FIG. 1. Slide member 40 is shifted forwardly along arm 12 to the position illustrated in dot-dash outline in FIG. 1. This slides needle driving member 36 to its extended position as is illustrated in FIG. 3. With the driving member extended, the leg portions 42a, 42b of needle gripping member 42 are spread apart. The shank of a needle 28 having a thread 32 secured thereto is inserted between leg portions 42a, 42b. Slide member 40 then is retracted to its position illustrated in solid outline in FIG. 4, thus retracting the needle driving member to the position illustrated in FIG. 4. Such retraction causes leg portions 42a, 42b of the gripping member to grasp the needle and draw it into channel 26 to the loaded position illustrated in FIG. 4. As the needle is drawn into the channel, thread 32 may follow therewith and extend outwardly from the channel through slot 30.

With the operating ends 12a, 14a of the device spread apart, tissue to be sutured is placed between the open end of channel 26 in operating arm 12a, and tissue shifting member 84. Swinging of finger ring portions 20, 22 toward each other brings the operating ends of the arms into engagement with opposite sides of the tissue to hold it therebetween, with such tissue being illustrated in dot-dash outline and indicated at 90 in FIGS. 4 and 5. In this position, needle 28 is aligned with and directed toward chamber 46.

Figure 6:
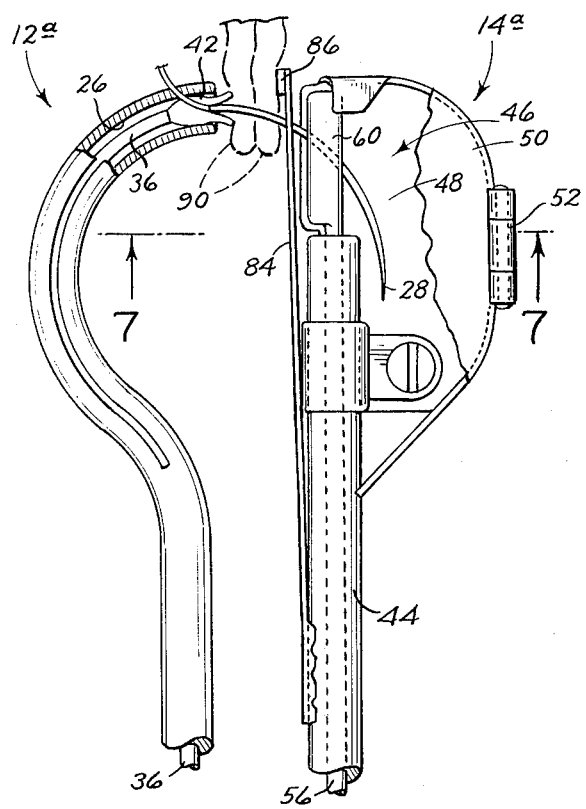
FIG. 6 is a view somewhat similar to FIG. 4, but with a needle in the device driven from one of the operating arms through tissue and into the other operating arm.

To drive the needle through tissue 90 the operator forces slide member 40 forwardly to the position illustrated in dot-dash outline in FIG. 1, which extends the needle driving member to shove the needle through the tissue and into chamber 46 as illustrated in FIGS. 6 and 7. Should the operator, in mid-stroke, wish to retract the needle and withdraw it from the tissue, he may do so merely by retracting slide member 40 which, because of needle gripping member 42 still grasping the shank of the needle, produces retraction of the needle back into channel 26.

When the needle has been driven fully from channel 26 as illustrated in FIG. 6, and into chamber 46, leg portions 42a, 42b of the gripping member spread apart to release the needle and operating lever 70 is manually rotated to shift holding member 60 from its release to its holding position, as illustrated in FIG. 7 gripping the needle and holding it in chamber 46. As has been mentioned previously, the coaction of spring 74 urging lever 70 forwardly, and the sloping surface of camming member 76 operate to yieldably bias holding member 60 to its holding position, thereby to assure a continuous gripping action by the holding member even if the user should release his force on the operating lever.

With the needle thus held in chamber 46, the operating ends of the arms are spread apart as illustrated in FIG. 8, thus to pull the needle fully through the tissue. To assure that the needle passes fully through the tissue, tissue engaging member 84, biased away from chamber 46, urges the tissue to pass fully over the shank of the needle, as is illustrated in FIG. 8.

The device then may be withdrawn from the area of the tissue, with thread 32 passing therethrough. The needle then may be reloaded in channel 26 for making another pass through the tissue, or a new needle may be loaded therein to pass another thread through the tissue.

Referring to FIG. 11, a device similar to that previously described is illustrated generally at 10 with modified tissue shifting mechanism thereon indicated generally at 100. Tissue engaging, or shifting, mechanism 100 includes an elongate member 102 pivotally connected intermediate its ends at 104 on arm 14. Member 102 includes a pair of elongate laterally spaced, substantially parallel side portions 102a, 102b extending along opposite sides of arm 14 and pivoted for swinging about pivot 104 in parallel planes past opposite sides of arm 14. The forward end 102c is positioned adjacent the opening between previously described edge margins 48a, 50a of needle receiving chamber 46, and has an opening therein through which a needle may pass from operating end 12a to operating end 14a of the arms into chamber 46.

The opposite, or rear, end portions 102d, 102e of member 102 are curved as illustrated in FIG. 10 and are positioned to swing part opposite sides of a midportion of arm 12 when pivoted about connection 104.

A spring arm 106 is received at its rear end to member 102 and at its forward end engages arm 14, urging member 102 to swing in a clockwise direction about pivot point 104. Forward end portion 102c of the member engages edge margins 48a, 50a of walls 48, 50, whereby the member normally is at rest in the position illustrated in FIG. 11. The member 102, however, may be swung, against the yieldable biasing force of spring 106 to rotate in a counterclockwise direction, as illustrated in FIG. 13, away from side walls 48, 50 and in the direction of operating end 12a of arm 12.

Secured to, and movable with, slide member 40 on arm 12 is an elongate rigid member 110. Member 110 is mounted for sliding movement longitudinally along arm 12 with member 40 between the position illustrated in solid outline in FIG. 11 when member 40 is drawn to its rearmost position to retract the needle driving member in the device, and forwardly along arm 12 to the position illustrated in FIGS. 12 and 13. It will be noted that in its retracted position, as illustrated in FIG. 11, member 110 is disposed completely rearwardly of rear ends 102d, 102e of member 102, and in its forwardmost position as illustrated in FIG. 12 and 13 it is adjacent ends 102d, 102e of member 102.

Describing the operation of tissue pushing mechanism 100, and referring to FIGS. 11—13, in sequence, initially with a needle retracted into the device and slide member 40 retracted, as illustrated in FIG. 11, spring 106 maintains member 102 in the at-rest position illustrated with its forward end 102c held against marginal edge portions 48a, 50a of chamber 46 to facilitate entry of tissue 90 between it and operating end 12a of arm 12 when the arms are swung apart. Following insertion of tissue 90 between the operating ends of the arms, the arms are swung together, as illustrated in FIG. 12, and slide member 40 is pushed forwardly along arm 12 to drive needle 28 through the tissue and into chamber 46. After the needle is driven through the tissue into chamber 46, needle holding member 60 is rotated to hold the needle in chamber 46. With member 40 slid forwardly along arm 12, member 110 comes into position adjacent rear end a 102d, 102e, of member 102. Thus, upon swinging of the arms to their open positions as illustrated in FIG. 13, member 110 engages rear ends 102d, 102e and forces the same to swing in a counterclockwise direction relative to operating end 14a of arm 14 to shove tissue 90 fully over the shank portion of needle 28.

A device as described herein is particularly well adapted for use by surgeons when working in regions of difficult accessibility and in places where visibility may be obscured. With such device, the surgeon need not have a clear view of the tissue to be sutured, but can be assured that once the operating ends of the arms are placed in engaging relationship on opposite sides of the tissue to be sutured, and the device is operated as above described, that the needle will be passed positively through the tissue, held in the chamber, and may be withdrawn with the assurance that the thread passed through the tissue. This also assures that the needle will be passed through the tissue with the device maintaining control of the needle throughout the operation whereby sewing can be done in a region of obscured visibility, without risk of loss of an unseen needle.

Of particular advantage in the device described are the features which allow the user to select at which stage of the operation he wishes to grasp the needle as it is passed through the tissue and allows the user to retract the needle, even if in mid-stroke. The first of these features is provided by the selectively actuatable holding device for gripping a needle after it is passed into the needle holding region of chamber 46. The second feature is provided by the needle retracting member which grips and holds a needle while in channel 26 and permits selective retraction thereof if desired. Also of importance is the tissue engaging feature which assures that the tissue is forced completely past the shank of the needle before the needle is withdrawn from the area of the tissue.

While a preferred embodiment of the invention has been described herein, it should be apparent to those skilled in the art that variations and modifications are possible without departing from the spirit of the invention.

It is claimed and desired to secure by Letters Patent:

1. A suturing device comprising
a pair of elongate, pivotally interconnected arms having a set of ends spaced from said pivot connection which are movable toward and away from each other for receiving tissue to be sutured therebetween and engaging opposite sides of said tissue and handle portions spaced from said ends for gripping by a user,
needle holding means on one of said arms for holding a needle with its point directed toward the other arm,
needle driving means on said one arm for driving said needle through tissue held between said arms and into a needle receiving region adjacent said other arm,
needle receiving means on said other arm in said needle receiving region,
holding means on said other arm for selectively engaging and holding a needle received in said needle receiving means, including a holding element mounted for selective shifting between a released position permitting free movement of a needle into and out of said needle receiving means and a holding position in which said needle is held in said receiving means to accommodate drawing the same through tissue on movement of said arms away from each other, and
an operator member mounted for rotational movement adjacent one of said handle portions and operatively connected to said holding element whereby rotating of said operator member between a released position and a holding position produces shifting of said holding element between its released and holding positions, and biasing means operatively connected to said operator member for yieldably urging said operator member and holding member toward their holding positions following initial displacement of said operator member from its released position.

2. The device of claim 1, which further comprises releasable catch means operable to impede initial displacement of said operator member from its released toward its holding positions.

3. A suturing device comprising
a pair of elongate, pivotally interconnected arms having a set of ends spaced from said pivot connection which are movable toward and away from each other for receiving tissue to be sutured therebetween and engaging opposite sides of said tissue, and handle portions spaced from said ends for gripping by a user, needle holding means on one of said arms for holding a needle with its point directed toward the other arm, needle driving means on said one arm for driving said needle through tissue held between said arms and into a needle receiving region adjacent said other arm, needle receiving means on said other arm in said needle receiving region, and holding means on said other arm for selectively engaging and holding a needle received in said needle receiving means, said holding means including a holding member mounted for rotation about a pivot axis which extends substantially longitudinally of its associated arm and is spaced laterally of said needle receiving region, said holding member having a lobe projecting outwardly from said pivot axis which is rotatable into and away from said needle receiving region, an operator member mounted adjacent one of said handle portions for rotation about an axis extending substantially longitudinally of said arm, and transmitting means interconnecting said holding and operator members for transmitting rotational motion therebetween, said holding means being selectively shiftable between a released position permitting free movement of a needle into and out of said needle receiving means and a holding position in which said needle is held in said receiving means to accommodate drawing the same through tissue on movement of said arms away from each other.

4. A suturing device comprising a pair of elongate, pivotally interconnected arms having a set of ends spaced from said pivot connection which are movable toward and away from each other for receiving tissue to be sutured therebetween and engaging opposite sides of said tissue, needle holding means on one of said arms for holding a needle with its point directed toward the other arm, said needle holding means including means defining an elongate needle storing channel open at an end thereof directed toward said holding means, needle driving means on said one arm for driving said needle through tissue held between said arms and into a needle receiving region adjacent said other arm, said needle driving means being shiftable in said channel between a retracted position spaced inwardly from said end and an extended position adjacent said end, needle retracting means operatively connected to said driving means for movement therewith between its retracted and extended positions operable to receive a shank portion of a needle and to grip the same to draw the needle into said channel on retraction of said needle driving means and to release its grip on said needle on shifting of said driving means to its extended position, needle receiving means on said other arm in said needle receiving region, and holding means on said other arm for selectively engaging and holding a needle received in said needle receiving means, said holding means being shiftable between a released position permitting free movement of a needle into and out of said needle receiving means and a holding position in which said needle is held in said receiving means to accommodate drawing the same through tissue on movement of said arms away from each other.

5. The device of claim 4, wherein said needle retracting means comprises a pair of oppositely disposed clip arms connected to said needle driving means, which arms are yieldably biased laterally outwardly from each other, whereby the same spread apart to receive a needle therebetween when said driving means is extended, and are forced toward each other by said means defining said channel on retraction of the driving means, thus to grip a needle therebetween.

6. The device of claim 4, wherein said means defining said channel comprises an elongate tubular member having an elongate slot extending through a side thereof longitudinally of the member for receiving of thread attached to a needle.

7. A suturing device comprising a pair of elongate, pivotally interconnected arms having a set of ends spaced from said pivot connection which are movable toward and away from each other for receiving tissue to be sutured therebetween and engaging opposite sides of said tissue, needle holding means on one of said arms for holding a needle with its point directed toward the other arm, needle driving means on said one arm for driving said needle through tissue held between said arms and into a needle receiving region adjacent said other arm, said needle driving means including a driving member mounted for movement against the shank of a needle held in said needle holding means toward and away from said other arm, manually operable actuating means mounted for movement on said one arm in a region spaced from said driving member between needle driving and needle retracting positions, and means operatively connecting said actuating means to said driving member for producing movement of the latter on operation of the former, needle gripping means on said driving means having opposed elements which open to receive a needle therein when said driving means is extended toward said other arm and which close on retraction of said driving member away from said other arm to grip said needle to retract the same into said needle holding means, needle receiving means on said other arm in said needle receiving region, and holding means on said other arm for selectively engaging and holding a needle received in said needle receiving means, said holding means being selectively shiftable between a released position permitting free movement of a needle into and out of said needle receiving means and a holding position in which said needle is held in said receiving means to accommodate drawing the same through tissue on movement of said arms away from each other.

8. A suturing device comprising a pair of elongate, pivotally interconnected arms having an adjacent set of ends swingable toward and away from each other for receiving tissue to be sutured therebetween and engaging opposite sides thereof, needle holding means on one of said arms including means defining a needle receiving channel having an open end directed toward said other arm for holding a needle with its point directed toward said other arm, needle driving means including a needle engaging element shiftable in said channel between an extended position adjacent said open end of the channel and a retracted position spaced inwardly along said channel from said open end, needle retracting means operatively connected to said driving means for movement therewith between its extended and retracted positions, said retracting means including means operable to receive a shank portion of a needle to grip the same and draw the needle into said channel on retraction of said needle driving means and to release said needle on shifting of said needle to its extended position, and manually operable actuating means mounted for movement in opposite directions on said one arm and spaced from said end of the arm, operatively connected to said driving means whereby movement of the actuating means in one direction produces extension of said engaging element to drive the element toward said other arm and movement in the opposite direction produces retraction of said element.

9. A suturing device comprising
a pair of elongate, pivotally interconnected arms having a set of ends spaced from said pivot connection which are movable toward and away from each other for receiving tissue to be sutured therebetween and engaging opposite sides of said tissue,
needle holding means on one of said arms for holding a needle with its point directed toward the other arm,
needle driving means on said one arm for driving said needle through tissue held between said arms and into a needle receiving region ajdacent said other arm, said needle driving means including a driving member mounted for movement against the shank of a needle held in said needle holding means toward and away from said other arm and actuating means for moving said driving member between an extended needle driving position and a needle retracting position, and
needle gripping means on said driving means having opposed elements which open to receive a needle therein when said driving means is extended toward said other arm and which close on retraction of said driving member away from said other arm to grip said needle to retract the same into said needle holding means.

10. A suturing device comprising
a pair of elongate, pivotally interconnected arms having a set of ends spaced from said pivot connection which are movable toward and away from each other for receiving tissue to be sutured therebetween and engaging opposite sides of said tissue,
needle holding means on one of said arms for holding a needle with its point directed toward the other arm,
needle driving means on said one arm for driving said needle through tissue held between said arms and into a needle receiving region adjacent said other arm,
needle receiving means on said other arm in said needle receiving region,
holding means on said other arm for selectively engaging and holding a needle received in said needle receiving means, said holding means being selectively shiftable between a released position permitting free movement of a needle into and out of said needle receiving means and a holding position in which said needle is held in said receiving means to accommodate drawing the same through tissue on movement of said arms away from each other, and
tissue shifting means interposed between said ends of the arms comprising a tissue engaging element mounted for movement with said other arm toward and away from said one arm and for movement relative to said other arm in the direction of said one arm, and biasing means urging said tissue engaging element to move from said other arm toward said one arm on spreading apart of said arms.

11. The device of claim 10, wherein said tissue engaging element comprises an elongate member disposed with one of its ends adjacent said end of the other arm, said end of the tissue engaging member being bifurcated to present laterally spaced legs disposed on opposite sides of a path along which a needle passes on being driven from said one arm toward said other arm.

12. A suturing device comprising
a pair of elongate, pivotally interconnected arms having a set of ends spaced from said pivot connection which are movable toward and away from each other for receiving tissue to be sutured therebetween and engaging opposite sides of said tissue,
needle holding means on one of said arms for holding a needle with its point directed toward the other arm,
needle driving means on said one arm for driving said needle through tissue held between said arms and into a needle receiving region adjacent said other arm, said needle driving means including a driving member mounted for movement against the shank of a needle held in said needle holding means toward and away from said other arm, manually operable actuating means mounted for movement on said one arm in a region spaced from said driving member between needle driving and needle retracting positions, and means operatively connecting said actuating means to said driving member for producing movement of the latter on operation of the former,
needle receiving means on said other arm in said needle receiving region,
holding means on said other arm for selectively engaging and holding a needle receiving in said needle receiving means, said holding means being selectively shiftable between a released position permitting free movement of a needle into and out of said needle receiving means and a holding position in which said needle is held in said receiving means to accommodate drawing the same through tissue on movement of said arms away from each other, and
tissue shifting means interposed between said ends of the arms including a tissue-engaging element mounted on said other arm for movement therewith toward and away from said one arm and for movement relative to said other arm in the direction of said one arm, and shifting means operable to produce shifting of said tissue-engaging element from said other arm toward said one arm on moving said arms apart with said actuating means moved to its said needle-driving position.

13. The device of claim 12, wherein said tissue-engaging element comprises an elongate pusher member pivotally connected intermediate its ends to said other arm and said shifting means comprises a member operatively connected to said actuating means and shiftable therewith between an operative position when said actuating means is in its needle-driving position for engaging and swinging said pusher member about said pivot connection when said arms are spread apart and an inoperative position out of engagement with said pusher member when said actuating means is in its needle-retracting position.

14. The device of claim 12, which further comprises biasing means yieldably urging said tissue-engaging element toward said other arm.

* * * * *